(12) United States Patent
Alito et al.

(10) Patent No.: US 8,906,388 B2
(45) Date of Patent: Dec. 9, 2014

(54) **METHODS FOR DETECTING *MYCOBACTERIUM TUBERCULOSIS* ANTIGENS**

(75) Inventors: Alicia Elsa Alito, Cuidad Autonoma de Buenos Aires (AR); Elisa Bernardina Spolsky, Cuidad Autonoma de Buenos Aires (AR); Monica Virginia Pontino, Cuidad Autonoma de Buenos Aires (AR)

(73) Assignee: Instituto Nacional de Tecnologia Agropecuaria (INTA), Ciudad Autonoma de Buenos Aires (AR)

( * ) Notice: Subject to any disclaimer, the term of this patent is extended or adjusted under 35 U.S.C. 154(b) by 0 days.

(21) Appl. No.: 13/460,914

(22) Filed: May 1, 2012

(65) Prior Publication Data

US 2012/0283118 A1    Nov. 8, 2012

(30) Foreign Application Priority Data

May 6, 2011    (AR) .............................. 20110101583

(51) Int. Cl.
*A61K 39/04* (2006.01)
*G01N 33/53* (2006.01)
*A61K 39/02* (2006.01)
*G01N 33/569* (2006.01)

(52) U.S. Cl.
CPC .................................. *G01N 33/5695* (2013.01)
USPC .................. 424/248.1; 424/184.1; 424/130.1; 424/168.1; 424/234.1; 435/4; 435/7.1; 435/7.2

(58) Field of Classification Search
USPC .......... 424/184.1, 130.1, 168.1, 234.1, 248.1; 435/4, 7.1, 7.5
See application file for complete search history.

(56) References Cited

PUBLICATIONS

Fournie, J.-J., et al. Journal of Biological Chemistry. vol. 266, No. 2, pp. 1211-1219, 1991.*

* cited by examiner

*Primary Examiner* — Rodney P Swartz
(74) *Attorney, Agent, or Firm* — Depillo & Associates, Inc.; Evelyn A. Defillo (57) ABSTRACT

Method for detecting *M. tuberculosis* antigens, comprising: a) contacting a sample of a biological fluid with a solid support; b) adding an amount of a first antibody against at least one *M. tuberculosis* protein; c) screening for the presence of *M. tuberculosis* proteins in the biological fluid by adding an amount of a second antibody which binds to the first antibody, in a Miniblotter device.

15 Claims, 6 Drawing Sheets

METHODS FOR DETECTING MYCOBACTERIUM TUBERCULOSIS ANTIGENS

CROSS REFERENCE TO RELATED APPLICATION

This application claims priority over Argentinean Patent Application No. 20110101583 filed May 6, 2011.

FIELD OF THE INVENTION

The present invention refers to a method for detecting *M. tuberculosis* antigens, comprising: a) contacting a sample of a biological fluid with a solid support; b) adding an amount of a first antibody against at least one *M. tuberculosis* protein; c) screening for the presence of *M. tuberculosis* proteins in the biological fluid by adding an amount of a second antibody which binds to the first antibody, in a Miniblotter device.

BACKGROUND OF THE INVENTION

Traditionally, direct diagnosis of *tuberculosis* relies on microbiological techniques such as microscopic examination (relatively fast but of low sensitivity) and on culture isolation which, in addition to being labor-intensive, requires an extended incubation period. Currently there exist new methods for a faster detection of mycobacteria but they are too expensive to be used in developing countries. In the field of Molecular Biology, the methods require a high-complexity laboratory as well as trained personnel. Further, detection of mycobacterial DNA does not allow for distinguishing metabolically active bacteria from dead bacteria. In addition, it is a test of limited diagnostic use not only because it is prone to contamination at a technical level, but also because its use is limited to smear-positive respiratory specimens.

Worldwide, *tuberculosis* is considered as a re-emerging disease that remains a serious public health problem in many high prevalence countries. According to the World Health Organization, an important part of the world population has been in contact with the tuberculous bacillus and could potentially suffer from the disease over the next years (World Health Organization, Report on the *tuberculosis* epidemia, Geneve, Switzerland, World Health Organization; 1996). It has been estimated that around 8 million people are infected each year, of which 3 million actually develop the disease.

SUMMARY OF THE INVENTION

A method for detecting *M. tuberculosis* antigens, comprising:
a) contacting a sample of a biological fluid with a solid support;
b) adding an amount of a first antibody against at least one *M. tuberculosis* protein;
c) screening for the presence of *M. tuberculosis* proteins in the biological fluid by adding an amount of a second antibody which binds to said first antibody. The biological fluid is selected from the group consisting of plasma, serum, sputum, urine, pleural fluid, ascites fluid, cerebrospinal fluid, and broncho-alveolar lavages (BAL) or any biological fluid; and *M. tuberculosis* proteins may comprise PPD H, PPD B, PPD A, Rv2031c (HspX), Rv2624c, Rv2626c, Rv2628, Rv3747, Rv3133c (DosR), Rv3874 (CFP10), Rv3875 (ESAT-6), Rv1932 (TPX), Rv0652 (L7/L12) or combinations thereof.

A method for detecting circulating *M. tuberculosis* antigens, comprising:
a) placing a nitrocellulose membrane inside a Miniblotter device;
b) adding an amount of a biological fluid to the membrane;
c) rotating the membrane 90° and seeding an amount of a first antibody against at least one *M. tuberculosis* protein;
d) screening for the presence of *M. tuberculosis* proteins in the biological fluid by adding an amount of a second antibody which binds to said first antibody. The biological fluid is selected from the group consisting of plasma, serum, sputum, urine, pleural fluid, ascites fluid, cerebrospinal fluid, and broncho-alveolar lavages (BAL) or any biological fluid; and *M. tuberculosis* proteins may comprise PPD H, PPD B, PPD A, Rv2031c (HspX), Rv2624c, Rv2626c, Rv2628, Rv3747, Rv3133c (DosR), Rv3874 (CFP10), Rv3875 (ESAT-6), Rv1932 (TPX), Rv0652 (L7/L12) or combinations thereof.

DETAILED DESCRIPTION OF THE INVENTION

For purposes of the present invention, the terms "protein" and "antigen" have the same meaning as when they refer to molecules of mycobacterial origin, for example *M. tuberculosis*.

A modified MAPIA assay (Multiple Antigens Printed Immuno Assay) is used as comparative assay.

The MADA assay (Multiple Antigens Detected Assay) is an embodiment of the method of the invention.

A direct method for detecting *M. tuberculosis* proteins present in the plasma of individuals, for example humans, has now been developed.

The method is intended to detect *tuberculosis* by means of a new diagnostic approach in which the individual's immune system is not involved, which also allows for anticipating the evolution of the disease. The method of the invention rapidly identifies proteins (antigens) produced by the pathogen *M. tuberculosis*. Production of these proteins by the pathogen in the host means that the bacterium is metabolically active and, hence, reveals the presence of a current infection in the host.

The method of the invention, as opposed to indirect methods which evaluate the host's immune system response (antibodies, cytokines and intradermal reactions), screens for the presence of a product of the pathogen which is released by metabolically active mycobacteria. Accordingly, its detection is indicative of a current infection whereas the indirect methods are not able to define if it is a past or present infection.

Application of the present method allows for rapidly diagnosing infected individuals. When applied to monitoring diseased individuals it allows for obtaining data about patient's response to treatment, by analyzing the presence, or absence, of the pathogen. This is a fast way of monitoring patients under treatment.

When referred to animals, the invention is useful for detecting false positive or negative results from the intradermal test (intradermoreaction).

Proteins secreted by the pathogen are present in human or animal serum from infected individuals. Among these proteins are the antigenic proteins secreted by mycobacteria. Accordingly, detection of any of these proteins demonstrates that the mycobacteria are metabolically active.

The method of the invention is useful for identifying a current infection, and does not depend on the immune system response of the host. Mycobacteria secrete proteins when they are metabolically active, and this method is capable of detecting them. Accordingly, the presence of pathogenic secretory proteins in the host's plasma is indicative of a current infection.

Three diagnostic methods were compared:

Two of these methods are based on the response of the host to the pathogen (Tuberculin skin test or PPD) and on detecting antibodies in host plasma using the MAPIA assay). The third method comprises detecting proteins which are expressed "in vivo" in host plasma or serum by the pathogen (MADA or method of the invention).

The response to PPD was compared to the MAPIA and MADA assays in the healthy individuals. The APIA and MADA of the diseased individuals were compared to clinical diagnosis.

Figure 1:
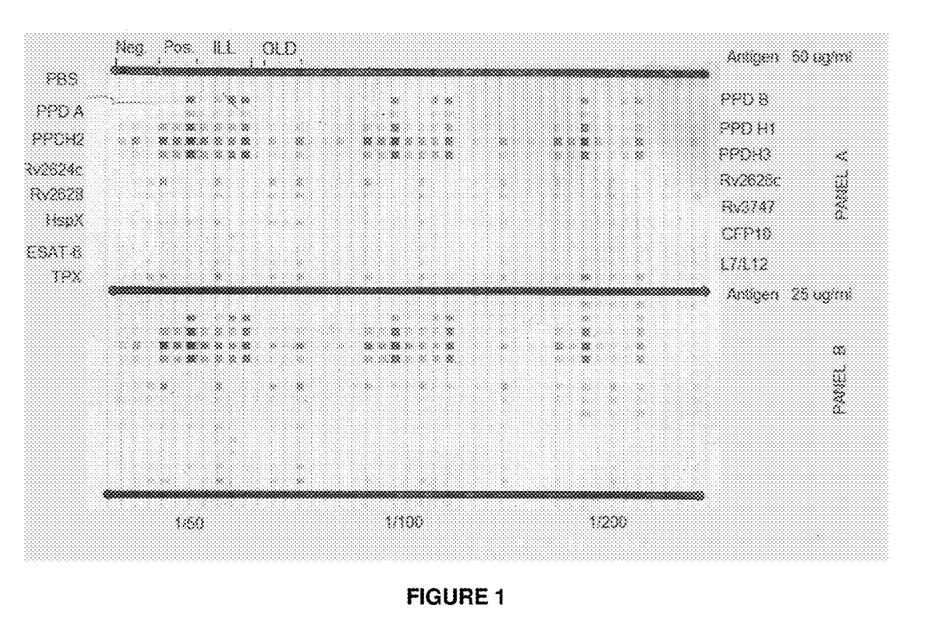
FIG. 1 shows the results of a MAPIA assay for determining minimum antigen concentration and maximum plasma dilution. Y axis: Details of the antigens. Panel A: Antigen concentration: 50 ug/mL. Panel B: Antigen concentration: 25 ug/mL. X axis: Three dilutions of human plasma: 1/50, 1/100, and 1/200.

The following was determined:

1. The minimum antigen concentration and maximum plasma dilution to be used in the MAPIA assay (FIG. 1). PPDs (PPDA, PPDB, PPDH1, PPDH2, and PPDH3) were seeded at two concentrations: 300 ug/mL and 150 ug/mL (panels A and B, respectively). Recombinant antigens were also seeded at two concentrations: 50 ug/mL and 25 ug/mL (panels A and B, respectively).

The individuals included in this test were randomly selected according to the following categories: 2 PPD-negative, 3 PPD-positive, 5 diseased (three under antibiotic therapy (TWT) and 2 samples taken before the patients started the treatment) (TBT) 2 under complete tuberculous treatment (CTT) and 2 with other pulmonary diseases (OPD). Three plasma dilutions were used: 1/50, 1/100, and 1/200. Selected concentrations were: PPDs (150 ug/mL), recombinant proteins (25 ug/mL) and for plasma a dilution of 1/50.

2. Minimum detection limit of each antigen simultaneously with mouse polyclonal antisera titer for the MADA test (FIG. 2, Tables I, II, and III)

The X axis reports antigen concentration at the different dilutions (Table I). The detected antigen mass is shown in Table III. On the Y axis the respective anti-recombinant protein antisera dilutions are indicated (Table I).

TABLE I

Figure 2:
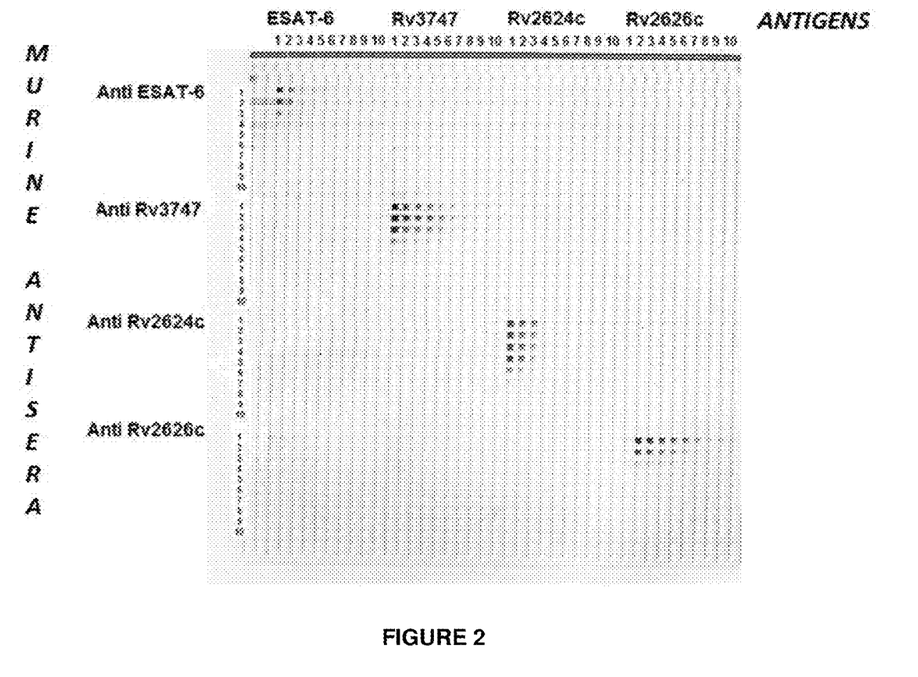
FIG. 2 shows antigen and antisera validation results. X axis: 1 to 10 decreasing concentrations of each antigen. Y axis: 1 to 10 antisera dilutions. Values used for antigens and antisera dilutions (25 ug/mL, 12.5 ug/mL, 6.25 ug/mL, 3.12 ug/mL, 1.56 ug/mL, 390 ng/mL, 97.65 ng/mL, 24.4 ng/mL, 6.1 ng/mL, 1.52 ng/mL).

Protein concentration and antisera dilutions used in FIG. 2

| | X axis pg/mL | | Y axis Antisera dilution | |
|---|---|---|---|---|
| 1 | $25 \times 10^6$ | 25 ug/mL | 1 | 1/1600 |
| 2 | $12.5 \times 10^6$ | 12.5 | 2 | 1/3200 |
| 3 | $6.25 \times 10^6$ | 6.25 | 3 | 1/6400 |
| 4 | $3.12 \times 10^6$ | 3.12 | 4 | 1/10000 |
| 5 | $1.56 \times 10^6$ | 1.56 | 5 | 1/20000 |
| 6 | $3.9 \times 10^9$ | 390 ng/mL | 6 | 1/40000 |
| 7 | $9.76 \times 10^4$ | 97.65 | 7 | 1/60000 |
| 8 | $2.44 \times 10^4$ | 24.41 | 8 | 1/80000 |
| 9 | $6.1 \times 10^3$ | 6.1 | 9 | 1/100000 |
| 10 | $1.5 \times 10^3$ | 1.52 | 10 | 1/120000 |

TABLE II

Results from FIG. 2

| PAR | X axis | Y axis |
|---|---|---|
| ESAT-6/ESAT-6 | anti 12.5 ug/mL | 1/3200 |
| Rv2624c/Rv2624c | anti 1.56 ug/mL | 1/6400 |
| Rv3747/Rv3747 | anti 6.25 ug/mL | 1/10000 |
| Rv2626c/Rv2626c | anti 390 ng/mL | 1/3200 |

X axis: Antigen detection limit.
Y axis: Antiserum title.

TABLE III

Results from FIG. 2 in mass units

| Antigen | Detection limit expressed as mass units |
|---|---|
| ESAT-6 | 31.25 ng |
| Rv2624c | 3.9 ng |

TABLE III-continued

Results from FIG. 2 in mass units

| Antigen | Detection limit expressed as mass units |
|---|---|
| Rv3747 | 15.62 ng |
| Rv2626c | 0.975 ng |

There is no cross-reaction among the different antigens of the antisera used (FIG. 2). In this assay, the minimum detection limit for each antigen is in the nanogram range. These results validate the antigens to be used in the MAPIA assay and the antisera for the MADA assay.

Figure 3:
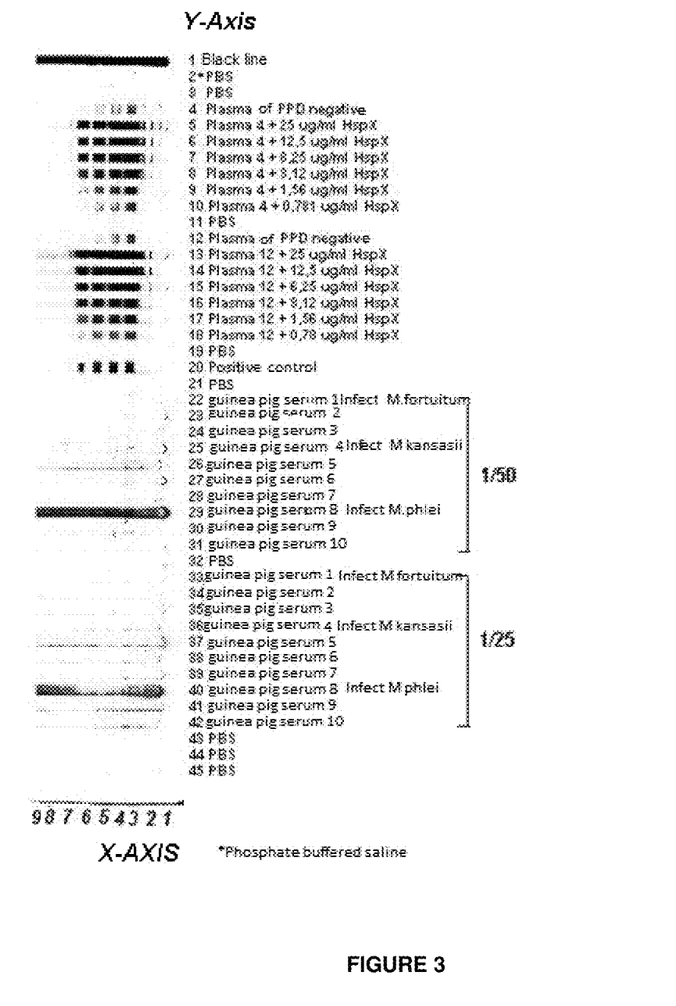
FIG. 3 shows minimum detection limit and specificity. X axis: 1, 2, 7, 8, 9 PBS-milk: 3, 4.5, and 6 anti-HspX at 1/25, 1/50, 1/100, 1/200 respectively. Y axis: 4 to 12 PPD-negative human plasma plus HspX at different concentrations (25 ug/mL, 12.5 ug/mL, 6.25 ug/mL, 3.12 ug/mL, 1.56 ug/mL, 0.78 ug/mL); 22 to 42 infected guinea pig sera with MNT dilutions of 1/25 and 1/50.

3. Minimum detection limit of (HspX) in plasma and its specificity (FIG. 3)

As HspX is the most frequent protein detected in plasmas of the tested individuals, its minimum detection limit in plasma was determined. HspX specificity was assayed using sera from guinea pigs infected with non-tuberculous mycobacteria (MNT). The minimum concentration detected in both plasmas corresponds to 6.2 ug/mL (Y axis: positions 7, 15). No HspX was detected at any of the dilutions employed with guinea pig sera. Color bands present at positions 29 and 40 (Y axis) are non-specific because they were also observed with control buffer (positions: 1, 2, 7, 8 and 9).

Comparison of MAPIA and MADA methods in humans

Figure 4:
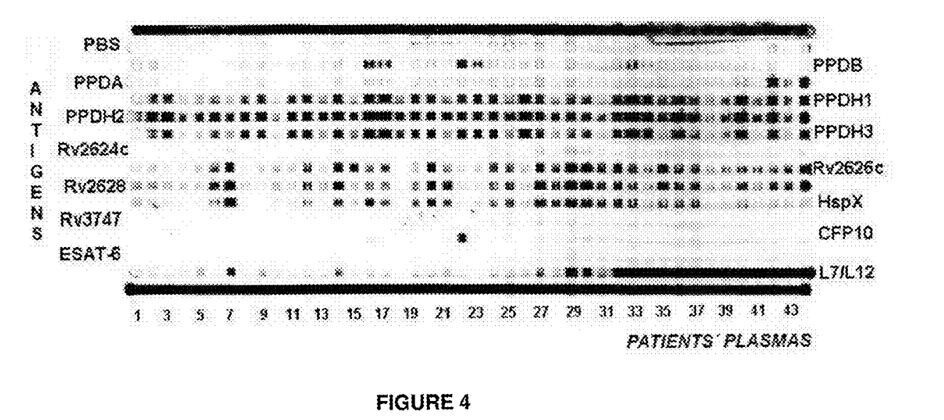
FIG. 4 shows the results for the Mapia assay in human plasma. 1 to 6, 8, 9, 12 to 14, 39, 43 PPD-negative; 7, 10, 11, 35, 38 PPD-positive; 18, 22, 23, 34 with *tuberculosis* before treatment (TBT); 16, 17, 20, 21 tuberculosis with treatment (TWT); 19, 24 to 29, 31 complete *tuberculosis* treatment (CTT); 15*, 30*, 32*, 33, 36, 37, 40*, 41 Other pulmonary diseases (OPD). *15, 30, 32, 40 patients with CTT and OPD

FIG. 4 shows recognition of antigens which are specific for *M. tuberculosis* by the host (MAPIA). According to the selection made with MAPIA of FIG. 1 a protein concentration (antigens) of 25 ug/mL and a plasma dilution of 1/50 were always used.

Figure 5:
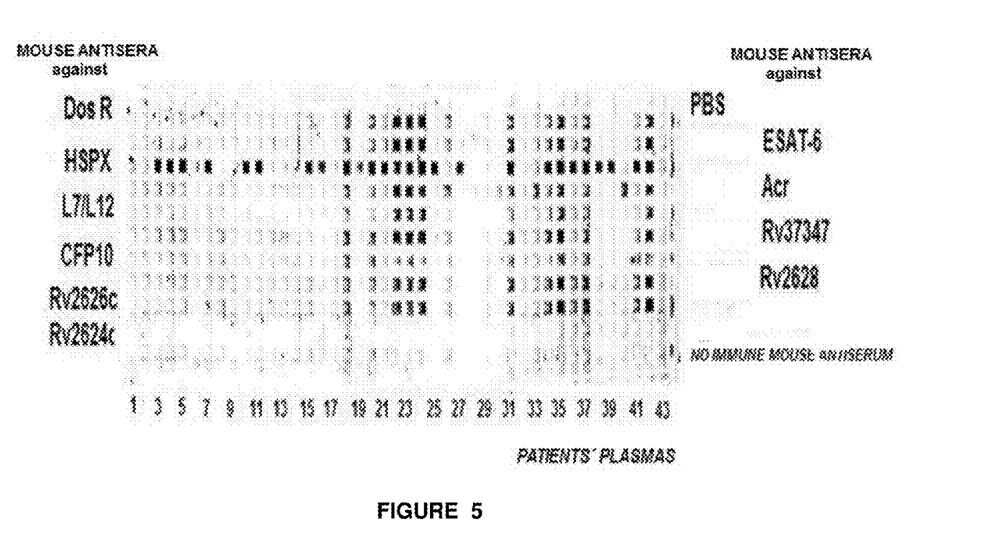
FIG. 5 shows the results for the Mada assay in patient plasma. Y axis: plasma of individuals under study: 1 to 6, 8, 9, 12 to 14, 40 and 43 PPD-negative; 7, 10, 11, 36, and 39 PPD-positive; 18, 22*, 23*, 24, 35 TBT; 16, 17, 20, 21 TWT; 19, 25 to 30, 32 CTT; 15**, 31, 33, 34, 37, 38, 41, 42. Other pulmonary diseases (OPD). X axis: polyclonal anti-specific recombinant protein mouse antisera of *M. tuberculosis*. 22* and 23*. Samples taken at various time points of centrifugation from the same patient, **15, 31, 33, 41 patients with CTT and OPD.

FIG. 5 shows the results of detecting proteins (antigens) in host plasma (MADA).

MAPIA measures host anti-mycobacterial protein antibodies. The host must be an immunocompetent individual; on the contrary, the test result is negative. The result of this test is related to the immunological memory of the host; accordingly, it cannot distinguish past from present infections. In contrast, MADA directly detects mycobacterial proteins in the host, independently from its immune system's. This fact broadens field the of application to immunosupressed patients (HIV carriers, elderly individuals, treatment with corticoids, etc) and to paucibacillary cases (extrapulmonary tuberculosis and children suffering from pulmonary *tuberculosis*). It is indicative of current infection because the mycobacteria secrete proteins if they are metabolically active.

Table IV

Profile of anti-*M. tuberculosis* protein antibodies and *M. tuberculosis* antigens in a healthy host

TABLE IV

LIST OF HEALTHY INDIVIDUALS

| No. | PPD | PMAD | MADA | PMAP | MAPIA |
|---|---|---|---|---|---|
| 1 | Neg | 1 | None | 1 | ?PPDH, αRv2628 |
| 2 | Neg | 2 | None | 2 | ?PPDH, αRv2628, |
| 3 | Neg | 6 | None | 6 | ?PPDH, αRv2626c, αRv2628 |
| 4 | Neg | 8 | None | 8 | ?PPDH |
| 5 | Neg | 9 | None | 9 | ?PPDH |
| 6 | Neg | 12 | None | 12 | ?PPDH, αRv2626c, αRv2628 |
| 7 | Neg | 13 | None | 13 | ?PPDH |
| 8 | Neg | 14 | None | 14 | ?PPDH, αRv2626c, ?Rv2628, ?HspX, αL7/L12 |
| 9 | Neg | 39 | HspX | 39 | ?PPDH, αRv2626c |
| 10 | Neg | 43 | None | 43 | αPPDA, αPPDH, αRv2626c, αRv2628 |
| 11 | Neg | | 3 | HspX | 3 | αPPDH |
| 12 | Neg | | 4 | HspX | 4 | αPPDH |
| 13 | Neg | | 5 | HspX | 5 | αPPDH |
| 14 | Pos | | 7 | HspX | 7 | αPPDH, αRv2626c, αRv2628, αL7/L12 |
| 15 | Pos | | 10 | HspX | 10 | αPPDH pX, |
| 16 | Pos | | 11 | HspX | 11 | αPPDH |
| 17 | Pos | | 39 | HspX | 38 | αPPDH |
| 18 | Pos | | 36 | HspX | 35 | αPPDH, αRv2626c, αRv2628, αHspX |
| 19 | Pos | | | HspX | | NH |
| 20 | Pos | | | HspX | | NH |
| 21 | Neg | | | HspX | | NH |
| 22 | Neg | | | HspX | | NH |
| 23 | Neg | | | HspX | | NH |
| 24 | Pos | | | HspX | | NH |
| 25 | Neg | | | HspX | | NH |
| 26 | Neg | | | HspX | | NH |
| 27 | Neg | | | HspX | | NH |
| 28 | Neg | | | HspX | | NH |

NH: Not done
PMAD: position in FIG. 5 of MADA
PMAP: position in FIG. 4 of MAPIA

PPD-Negative

Thirteen of 20 individuals were tested by MAPIA and MADA (FIGS. 4 and 5). The remaining 7 individuals were only tested by MADA.

MAPIA: The 13 individuals showed antibodies against PPD (100%) and 7 of them (54%) against latency proteins MADA: The presence in plasma of HspX (55%) was detected in 11 of 20 individuals.

(Thirteen out of 20 individuals are represented in FIG. 5).

PPD-Positive

Five out of 8 individuals were tested using MAPIA and MADA (FIGS. 4 and 5). The remaining 3 were only evaluated by MADA.

MAPIA: Among the individuals, a 100% were positive to anti-PPD antibodies and 4 (80%) of them showed anti-latency protein antibodies (Table IV).

MADA: HspX was detected in the plasma of the 8 individuals (100%). Five out of 8 individuals are represented in FIG. 5.

In MAPIA, the antibody profile is similar in PPD-negative and -positive individuals. Further, in MADA among all assayed antigens only one was detected (HspX) which is present in 100% of PPD-positive individuals and in 55% (11/20) of PPD-negative individuals. *Possibly, the antigen-antibody reaction occurring in our test is more sensitive than the late hipersensitivity reaction (Tuberculin test or Mantoux reaction or PPD or intradermoreaction) and there may be false negatives in the group of PPD-negative individuals. The other factor to consider would be the anergy of some individuals which may mask the result of the Mantoux reaction but not of MADA.

Using the values shown in table IV, Test Sensitivity and Specificity was determined (it should be considered that n is low and the test of reference (PPD) is not good) for the HspX antigen:

|       | PPD+ | PPD- |    |
|-------|------|------|----|
| MADA+ | 8    | 11   | 19 |
| MADA− | 0    | 9    | 9  |
|       | 8    | 20   | 28 |

Sensitivity: 100%

Specificity: 45%*

Profile of anti-*M. tuberculosis* protein antibodies and *M. tuberculosis* proteins in patients Tuberculosis Before Treatment (TBT)

MAPIA: Four patients (100%) showed anti-antibodies PPD in plasma, 3 (75%) showed anti-latency proteins antibodies and 1 (25%) showed anti-CFP10 antibodies (FIG. 4, Table V).

MADA: All antigens except for Rv2624c were detected by MADA (see FIG. 5 and Table V)

Tuberculosis with Treatment (TwT)

MAPIA: Four patients (100%) showed anti-PPD antigen antibodies and against latency antigens (see FIG. 4 and Table V).

MADA: In three patients (75%) HspX was detected and in the remaining patient (25%) a detection profile similar to TBT was found (see FIG. 5 and Table V).

Complete *Tuberculous* Treatment (CTT)

MAPIA: Eight patients (100%) showed anti-PPD antibodies and 7 (87%) anti-latency antigen antibodies (FIG. 4 and Table V).

MADA: HspX was detected in four patients (50%). (see FIG. 5 and Table V).

Other Pulmonary Diseases (OPD)

MAPIA: Eight patients (100%) showed anti-PPD and anti-Rv2626c antibodies; 7 patients had anti-Rv2628 antibodies (87%) and 3 patients anti-HspX antibodies (37%) (FIG. 4 and Table V)

MADA: In three patients (37%) the presence of HspX was detected in plasma and in the rest all antigens under study were detected except Rv2624c. (see FIG. 5 and Table V)

MAPIA shows an antibody profile which is similar in the 4 sequences of presented states (TBT, TWT, CTT, and OPD). Accordingly, it appears that it is not able to distinguish patients without treatment from patients with treatment. On the contrary, MADA detects diseased individuals by means of a multiantigenic profile of antigen detection. This is observed in the TBT group. This type of profile could be characteristic of non-treated *tuberculosis* and could be indicating metabolically active mycobacteria.

Three of the four TWT responded well to the treatment except for patient 9 (Table V). The latter shows an antigen profile similar to that of TBT. This result would suggest that the patient is responding very slowly to the therapy or that the disease is an extra-pulmonary *tuberculosis* (data not collected) which evolves slowly.

Patients of the CTT group have an antigen profile which is similar to that of a good response to therapy and to that of healthy individuals.

Out of the 8 individuals OPD, four (15, 20, 22, 23 Table V) had suffered from *tuberculosis* in the past. One (20, Table V) among the latter group was admitted at the hospital through the Emergency Room, as well as other three patients (5, 6, and 7 Table V) which had not suffered from TB in the past. The remaining patient (24 in Table V) is the contact of a *tuberculosis* focus at his workplace. HspX was detected in two who had *tuberculosis* in the past (15 and 23) and in the contact (24). The five remaining patients show a multiantigenic profile by MADA.

TABLE V

RELATIONSHIP BETWEEN CLINICAL SYMPTOMATOLOGY AND MAPIA AND MADA TESTS

| No. | Category | Diagnosis | Thorax X-Ray * | Clinical symptomatology | MADA | MAPIA |
|-----|----------|-----------|----------------|-------------------------|------|-------|
| 1 | TBT | TB | Bilateral cavitated tuberculosis | No expectoration. Feels tired since two months ago. | Rv2626, Rv2628, Rv3747. ESAT-6, L7/L12. | αPPDB, αPPDA, αPPDH, αEST-6, αCFP10. |
| 2 | TBT | TB | Bilateral biapical infiltrates with prevalence in the right | Lost weight in 2 months. Dry cough. No catarrh. Night sweating. | Rv2626, Rv2628, Rv3747, ESAT-6, L7/L12. | αPPDB, αPPDA, αPPDH. |
| 3 | TBT | TB | TB diagnosed a year and a half ago. Three abandonment. No treatment since 3 months. | Sweating Positive smear. Cough with expectoration. | HspX, CFP10, ESAT-6 | αPPDH. |
| 4 | TBT | Hemoptysis without decompensation | Tenuous infiltrate. | Dry cough. Hemoptic sputum. TB to be discarded. | Rv2626, Rv2628, Rv3747, ESAT-6, L7/L12, DosR | αPPDH. |
| 5 | OPD | OPD | Pulmonary emphysema | Hypoventilation. | Rv2626, Rv2628, HspX, Rv3747, | αPPDH, αRv2626c, αRv2628. αHspX. |

TABLE V-continued

RELATIONSHIP BETWEEN CLINICAL SYMPTOMATOLOGY AND MAPIA AND MADA TESTS

| No. | Category | Diagnosis | Thorax X-Ray * | Clinical symptomatology | MADA | MAPIA |
|---|---|---|---|---|---|---|
| 6 | OPD | Acute bacterial super-infection (OPD) | Apical fibrosis | Hypoventilation. COPD. Isolation of Aspergillus llus. Afebrile. Sputum: abundant yeasts. | CFP10, ESAT-6, L7/L12, DosR. Rv2626c, Rv2628, HspX, CFP10, Rv3747, ESAT-6, L7/L12. | αPPDB, αPPDH, αRv2626c, αRv2628. |
| 7 | OPD | Respiratory infection (OPD) | Bilateral infiltrates with apical prevalence. | Severe malnutrition. Effective cough. Whitish expectoration. Negative smear. Diabetic. | Rv2626, Rv2628, HspX, Rv3747, ESAT-6, CFP10, L7/L12, DosR. | αPPDH, αRv2626c, αRv2628, αHspX. |
| 8 | TWT | TB | Sequel to lungs due to TB. | TB 12 years ago. Hospitalized for bronchial pneumonia. Positive smear. Treatment with antibiotics. | HspX | αPPDH, αRv2626c, αRv2628, αHspX. |
| 9 | TWT | TB relapse | Bilateral infiltrates. | Two months of treatment with antibiotics. TB 40 years ago. | Rv2626, Rv2628, HspX, Rv3747, ESAT-6, CFP10, L7/L12. | αPPDH, αRv2626c, αRv2628, αHspX. |
| 10 | TWT | TB | Bilateral tuberculosis | Under treatment for 4 months | None | αPPDB, αPPDH, αRv2626c, αRv2628, αHspX |
| 11 | TWT | TB | Bilateral tuberculosis | Under treatment for 4 months. | HspX | αPPDB, αPPDA, αPPDH, αRv2626c, αRv2628, αHspX. |
| 12 | CTT | Presumptive TB | A year with image compatible with TB. Current X-ray normal. | Finished treatment 6 months ago. Negative smear and negative culture. | HspX | αPPDH, αRv2626c, αRv2628, αHspX. |
| 13 | CTT | ExTB | Pulmonary fibrosis | ExTB. Had TB when 3 years old. Thirty seven years ago. Comes for control. | HspX | αPPDH, αRv2626c, αRv2628, αHspX. |
| 14 | CTT | ExTB OPD | Pulmonary emphysema | TB 20 years ago. | HspX | αPPDH, αRv2626c, αRv2628, αHspX. |
| 15 | OPD | Pneumonia | Typical TB sequels. Right lung very compromised and fibrous. PI with hyperinsufflation. | No weight loss. Has catarrh. Bronchiectasis. Negative smear. Possibly ex-tuberculous. | HspX | αPPDH, αHspX, αRv2626c, |
| 16 | CTT | OPD | Important sequels in lungs. | ExTB. Decreased lung capacity. Negative smear and culture. Respiratory wheezing. | HspX | αPPDB, αPPDH. |
| 17 | CTT | OPD | No type of sequels. | Five years ago had pulmonary and extrapulmonary TB. Six months of treatment. Currently has bronchitis. | None | αPPDH, αRv2626c, αRv2628, αHspX, αL//L12. |
| 18 | | Presumptive ExTB | Sequels in both lung vertices (scars) | TB focus (pac1) at the workplace. | None | αPPDH, αRv2626c, αRv2628, αHspX. |
| 19 | CTT | ExTB | Normal X-ray. | TB 22 years ago. Comes for control. | None | αPPDH, αRv2626c, αRv2628, αHspX, αL7/L12. |

TABLE V-continued

RELATIONSHIP BETWEEN CLINICAL SYMPTOMATOLOGY AND MAPIA AND MADA TESTS

| No. | Category | Diagnosis | Thorax X-Ray * | Clinical symptomatology | MADA | MAPIA |
|---|---|---|---|---|---|---|
| 20 | OPD | ExTB | TB 17 years ago. TB sequels. Lung with liquid or air. | Entered through Emergency Room. Could not breathe. | Rv2626c, Rv2628, HspX, Rv3747, ESAT-6, L7/L12. | αPPDH, αRv2626c, αRv2628, αHspX, αL7/L12. |
| 21 | CTT | ExTB | Normal X-ray. | Hospital-acquired TB. Completed treatment 3 years ago. | None | αPPDH, αRv2626c, αRv2628, αHspX, αL7/L12. |
| 22 | OPD | COPD | Acute pulmonary emphysema. Lungs with cavities. | Weight Loss Had TB 22 years ago. | Rv2626c, Rv2628, HspX, Rv3747, ESAT-6, CFP10, L7/L12. | αPPDB, αPPDA, αPPDH, αRv2626c, αRv2628 |
| 23 | OPD | COPD | Right vertex opacity. | Had positive smear a year ago. Anti-TB treatment. Emphysematous. | HspX | αPPDH, αRv2626c, αRv2628, αHspX |
| 24 | OPD | OPD | Hyperinsufflation | TB focus (pac1) at the workplace. | HspX | αPPDH, αRv2626c, αRv2628, αHspX |

All thorax X-ray data correspond to beginning of treatment for all patients.

6. Evidence of *Mycobacterium tuberculosis* HspX in Plasma of a PPD-Positive Individual.

Figure 6:
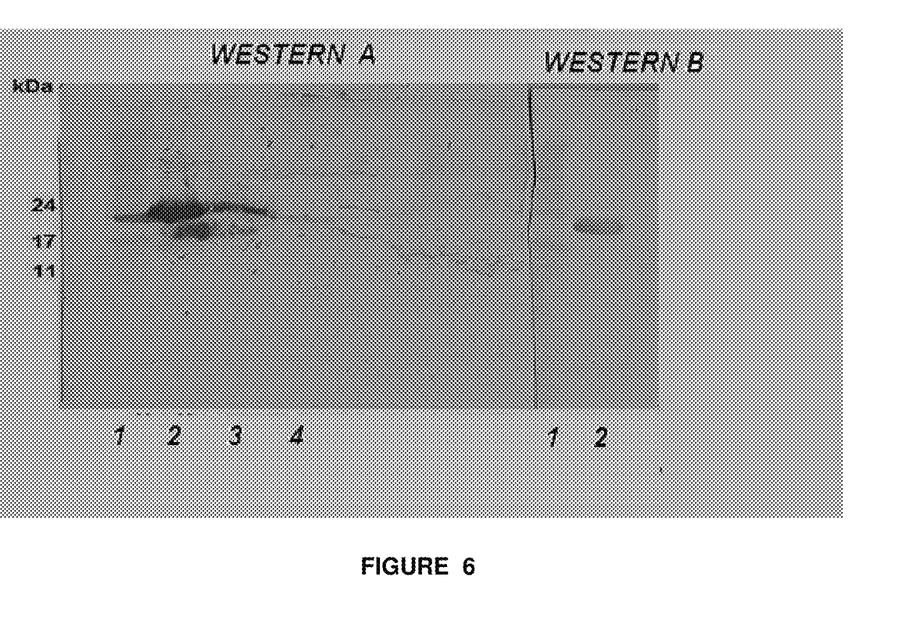
FIG. 6 shows that the selected antigen was HspX. Using the method of the present invention followed by Western, it was determined that the MW of the detected protein in plasma of a PPD-positive individual corresponds to the MW of that purified protein. Recombinant HspX antigen was seeded, 8 ug per line (lines 2 and 10, FIG. 6 Results). Dilutions: 1/1.6 and 1/25 of plasma from the PPD-positive individual (positions 3 and 4) were seeded. The molecular weight marker was seeded at positions 1 and 9. Electrophoresis and transfer conditions were: 90 volts for the former and constant current of 230 mA for 1 hour and 30 minutes for the latter. The presence of the protein was verified using Ponceau Red.

As the color reaction obtained in MADA corresponds to detection of each antigen it only indicates one antigen/antibody reaction. To verify if the reaction correlates with the MW of the detected protein, a PAGE-SDS was conducted with one of the most frequently detected antigens. The selected antigen was HspX. Using this method, followed by Western, it was determined that the MW of the detected protein in plasma of a PPD-positive individual corresponds to the MW of that purified protein (FIG. 6)

To the best knowledge of the present inventors, in the literature of TB diagnosis there are to references to direct detection of mycobacterial *M. tuberculosis* antigens in plasma without using double antibodies or a sandwich system The present method allows for a simultaneous multi-evaluation of plasmas and antigens. It is a simple, practical and rapid methodology.

This invention is better illustrated in the following examples, which should not be construed as limiting the scope thereof. On the contrary, it should be clearly understood that other embodiments, modifications and equivalents may be possible after reading the present description, which may be suggested to a person of skill without departing from the spirit of the present invention and/or the scope of the appended claims.

EXAMPLES

Example 1

Preparation of the Assays

Study Population:

Healthy population: Individuals belonging to the community grouped as follows: a) 20 individuals without detectable infection by Mantoux reaction and without a history of previous treatment or of having been in contact with the mycobacteria either for work-related reasons or for proximity to a person with TB. The latter are considered as negative controls. b) 8 healthy infected individuals (Mantoux reaction ≥10 mm without previous history of tuberculous infection or disease treatment). All the subjects of this group have recent chest X-ray with no evidence of active disease.

Adult patients attending the Acute and Chronics Zonal Hospital Dr. Cetrángolo, Vicente López, province of Buenos Aires. Patients were categorized according to intersection of two variables: treatment and moment of sampling. Four groups were thus obtained: a) 4 patients without treatment at the moment samples were taken (TBT) b) 4 patients under treatment at the moment samples were taken (TWT) c) 8 with complete tuberculous treatment (CTT), and d) 8 patients with other pulmonary diseases (OPD). Patients were clinically, radiologically and bacteriologically evaluated by pneumonologists and bacteriologists of that hospital.

Samples

Peripheral venous blood from individuals belonging to these populations. Blood was introduced into sterile tubes with sodium heparin Northia (25000 IU, 5 uM final concentration). Plasmas were separated by centrifugation. Plasmas were kept at minus 70° C. Work was carried out under sterile conditions to prevent any contamination.

Sera of guinea pigs infected with non-tuberculous mycobacteria (MNT): *M. kansasii*, *M. fortuitum*, and *M. phlei*. These sera were kindly provided by Dr. Susana Oriani from the School of Veterinary Sciences, National University of La Pampa (UNLP)

*M. tuberculosis* Proteins (Antigens)

*M. tuberculosis* native antigens and recombinant proteins used in the assays were: a) Purified protein derivatives (PPD) of *M. tuberculosis* PPD H, of *M. bovis* PPD B and of *M. avium* PPD A. The three PPD H (1, 2, and 3) were kindly provided by biochemist Claudia Argüelles of the National Administration of Laboratories and Health Institutes (Anlis) b) recombinant latency proteins markers: Rv2031c (HspX), Rv2624c, Rv2626c, Rv2628, Rv3747 and Rv3133c (DosR), c) recombinant proteins of early infection markers: Rv3874 (Culture Filtrate Protein or CFP10), Rv3875 (ESAT-6) d) secretion proteins with no defined function: Rv1932 (TPX) and L7/L12. These recombinant proteins were cloned according to the following protocols (Gioffré A, Caimi K, Zumárraga M J, Meikle V, Morsella C, Bigi F, Alito A, Santángelo M P, Paolicchi F, Romano M I, Cataldi A. A. (2006) Lpp34, a novel putative lipoprotein from *Mycobacterium avium* subsp. Paratuberculosis, *J Vet Med B Infect Dis Vet Public Health*, 2006 Feb; 53(1): 34-41). Briefly, all proteins were cloned into expression vectors bearing 6 genes encoding a polyhistidine in its sequence. When each mycobacterial protein gene mentioned in paragraph b is inserted into the expression vector, polyhistidine sequences are located downstream of the *M. tuberculosis* protein genes. Accordingly, each recombinant protein has 6 histidine (His) molecules at its carboxyl terminus which are used for binding to anti-His antibodies present in an agarose column and thus for its purification.

Most of the above-mentioned proteins are secretion proteins except for Rv2624c which is cytoplasmatic and Rv3747 which is a membrane protein.

Protein purification: it was carried out using the Ni-NTA agarose matrix (QIAGEN, 34450) and conventional methodology of this protocol was followed (The QIA expressionist-QIAGEN)

Protein quantification: It was performed using the Micro BCA Protein assay kit (Biodynamics, Cat. 23235) and Pierce's Bradford Reagent (Bio Rad Protein assay, Dye reagent concentrate, Cat. 500-0006)

Murine Antisera

Mouse anti-*M. tuberculosis* protein polyclonal antibodies were obtained from about 8-week old female Balb/c mice. Antisera for each antigen were obtained by dividing mice into groups of five. Each one was intraperitoneally injected with 0.2 mL of a suspension containing 15 ug of each protein and Freund's incomplete adjuvant at a 1:1 volume ratio. To this suspension 0.1% Tween 40 was added for solubilization. Two immunizations were performed with one week interval. By the end of each week, the corresponding bleeding was done to obtain the antisera. Then they were validated and titered.

Modified MAPIA (Multiple Antigens Printed Immuno Assay)

This methodology was used as a comparative control for recognizing the antibodies present in plasma samples of the above-mentioned healthy and diseased populations.

It was carried out in a mini transfer apparatus or Miniblotter which is an acrylic device (MN45; Immunetics, Cambridge, Mass.) having 45 channels of 2 mm in diameter by 12 cm in length with two orifices at both ends. Samples are seeded in the upper end orifices. Each channel has a capacity of 150 uL.

A 15×15 cm nitrocellulose membrane (NC) is placed on pads inside the Miniblotter. One hundred and fifty microliters (150 uL) of each antigen and control are seeded in the channels. Two hours later, seeded fluids are withdrawn using vacuum. The membrane is removed and blocked with PBS buffer plus 5% skimmed milk (PBS-milk). The NC is placed back in the Miniblotter but changing its orientation 90° and thereby the channels are orientated perpendicularly to the seeding lines pattern of previously seeded antigens and controls. Plasma samples are seeded. The system is incubated for two hours. After this, samples are removed and the NC is washed three times with PBS plus Tween 20. From here on, the classic procedure of a Western is performed. The NC is incubated with stirring for two hours with alkaline phosphatase-conjugated anti-human IgG ($1/150000$); after another washing cycle, the membrane developed using 5-Bromo-4-Chloro-3-Indolyl Phosphatase-Nitro Blue Tetrazolium (BCIP-NBT PIERCE PROTEIN, Cat. 34042). The reaction is stopped by adding bidistilled water, and the NC is allowed to air-dry.

The following antigen and plasma dilutions were used: PPD: 150 ug/mL; recombinant antigens: 25 ug/mL; plasma dilution: $1/50$ All washing procedures were carried out under constant stirring and incubations were performed at room temperature.

MADA (Multiple Antigens Detected Assay):

This is the preferred methodology of the invention and allows for a direct detection of the proteins secreted by *M. tuberculosis* into host mononucleated cells in plasma samples of the infected population. The secretion process of bacteria is an indication of their viability and hence of infection. This method is a new and rapid way of distinguishing healthy from infected populations.

The same Miniblotter (MN45) was used. First, 150 uL of plasma samples from patients are seeded on a nitrocellulose membrane. Then, 150 uL of each of the previously described murine antisera anti-mycobacterial proteins are seeded as a first antibody. The Minoblotter is only used for first seeding the plasmas and then the antisera with a rotation of 90° of the membrane between each application. As a second antibody, an alkaline phosphatase-conjugated to a mouse anti-complete IgG immunoglobulin (SIGMA, A 3562) is used. Dilution $1/150000$ in PBS-milk.

The blocking solution, washings, incubation times and development are the same as those described for MAPIA.

Plasma concentration and mouse antisera were: human plasma: $1/25$ and mouse anti-*M. tuberculosis* protein serum: $1/50$.

Example 2

Minimum Detection Limit of Antigens and Validation of Antisera

Using the MADA test, minimum detection limit of antigens and validation of antisera could be determined simultaneously. Serial dilutions of recombinant antigens in a range of 25ug/mL to $0.381 \times 10^{-3}$ ug/mL and mouse antisera dilutions of $1/1600$ to $1/120000$ were used. To determine the mass detected for each antigen three parameters were considered: seeded volume (150 uL), detection surface which is (2 mm×2 mm=4 mm$^2$), and considering that those 150 uL run over a membrane surface of 240 mm$^2$ (membrane length of 12 cm or 120 mm by a 2 mm width). After performing the respective calculations, the minimum detection limit indicated in Table III was determined.

Minimum Detection Limit of (HspX) in Plasma and its Specificity

Two plasmas from PPD-negative individuals in which this antigen had not been detected previously using the MADA test (FIG. 5, positions 1 and 2) were used. Plasmas were diluted 1/50. Different volumes of HspX, at final concentrations ranging from 25 ug/mL to 0.78 ug/mL, were added to each plasma. As a positive control, a 1/50 plasma dilution from a PPD-positive individual in which HspX was detected by MADA (FIG. 5, position 7) was employed.

With respect to specificity, MNT-infected guinea pig sera were used. Dilutions were: 1/25 and 1/50. Sera from 10 infected guinea pigs were used: 3 with *M. kansasii*, 3 with *M. phlei*, and 4 with *M. fortuitum*.

PAGE-SDS, Western Blot Followed by Immunoassay

The electrophoresis technique described by Laemmli in 1970 was used. Recombinant HspX antigen was seeded, 8 ug per line (lines 2 and 10, FIG. 6, Results). Dilutions: 1/1.6 and 1/25 of plasma from the PPD-positive individual (positions 3 and 4) were seeded. The molecular weight marker was seeded at positions 1 and 9. Electrophoresis and transfer conditions were: 90 volts for the former and constant current of 230 mA for 1 hour and 30 minutes for the latter. The presence of the protein was verified using Ponceau Red.

Conventional immunoassay steps were followed using a mouse anti-Histidine monoclonal antibody (lane 10 in the Western) and mouse anti-HspX antisera for lanes 1 to 4. As a second antibody, a complete goat anti-mouse IgG marked with alkaline phosphatase was used. It was developed with the chromogenic substrate BCIP/NBT. After identifying the occurrence of black purple colored bands having the adequate intensity, the reaction is stopped using an excess of distilled water. The membrane is dried with Whatman paper for its preservation.

Ethical and Environmental Safeguards

This study was carried out with the consent of the Ethics Committee of the Cetrángolo Hospital and with the informed consent of the individuals participating in the study. As the present proposal involves the medical field, the studies were performed according to the stipulated ethics, legal and judicial safeguards as established in the National Bioethic Standards—ANMAT Provision No. 5330/97—as well as International—NÜREMBERG Code, Declaration of Helsinki and modifications thereof, Universal Declaration on Human Genome and Human Rights approved by the General Conference of UNESCO of Nov. 11, 1997.

Having thus specifically described and determined the nature and the best mode for carrying out the present invention, it is declared as claimed property and of exclusive right:

The invention claimed is:

1. A method for detecting *M. tuberculosis* antigens comprising the steps of:
   a) contacting a sample of a biological fluid with a solid support;
   b) adding an amount of a first antibody against a *M. tuberculosis* protein, wherein the first antibody is specific for the *M. tuberculosis* protein, wherein said *M tuberculosis* protein is selected from the group consisting of PPD H, PPD B, PPD A, Rv2031c (HspX), Rv2624c, Rv2626c, Rv2628, Rv3747, Rv3133c (DosR), Rv3874 (CFP10), Rv3875 (ESAT-6), Rv1932 (TPX), and Rv0652 (L7/L12);
   c) washing off non-attached first antibodies;
   d) adding an amount of a marked second antibody which binds to said first antibody;
   e) washing off non-attached second antibodies; and
   f) screening for the presence of the *M. tuberculosis* protein in the biological fluid by adding reagents for detection of the marked second antibody.

2. The method according to claim 1, wherein said biological fluid is selected from the group consisting of plasma, serum, sputum, urine, pleural fluid, ascites fluid, cerebrospinal fluid, and broncho-alveolar lavage (BAL).

3. The method according to claim 1, wherein said first antibody is a mouse polyclonal antiserum.

4. The method according to claim 3, wherein said mouse antiserum is added at a dilution of 1/25, 1/50, 1/100, and 1/200.

5. The method according to claim 1, wherein said solid support is a nitrocellulose membrane.

6. The method according to claim 1, wherein said marker is selected from the group consisting of alkaline phosphatase, peroxidase, biotin, and chemiluminescence.

7. The method according to claim 2, wherein said biological fluid is plasma.

8. The method according to claim 1, wherein between step a) and b) non-specific binding sites to the solid support are blocked by incubating the solid support with non-specific proteins.

9. A method for detecting circulating *M. tuberculosis* antigens comprising the steps of:
   a) placing a nitrocellulose membrane inside a Miniblotter device;
   b) adding an amount of a biological fluid to the membrane;
   c) rotating the membrane 90° and seeding an amount of a first antibody against a *M. tuberculosis* protein, wherein the first antibody is specific for the *M tuberculosis* protein, wherein the *M. tuberculosis* protein is selected from the group consisting of PPD H, PPD B, PPD A, Rv2031c (HspX), Rv2624c, Rv2626c, Rv2628, Rv3747, Rv3133c (DosR), Rv3874 (CFP10), Rv3875 (ESAT-6), Rv1932 (TPX), and Rv 0652 (L7/L12);
   d) washing off non-attached first antibodies;
   e) adding an amount of a marked second antibody which binds to said first antibody;
   f) washing off the non-attached second antibodies; and
   g) screening for the presence of the *M. tuberculosis* protein in the biological fluid by adding reagents for detection of the marked second antibody.

10. The method according to claim 9, wherein said biological fluid is selected from the group consisting of plasma, serum, sputum, urine, pleural fluid, ascites fluid, cerebrospinal fluid, and broncho-alveolar lavage (BAL).

11. The method according to claim 9, wherein said first antibody is a mouse polyclonal antiserum.

12. The method according to claim 11, wherein said mouse antiserum is added at a dilution of 1/25, 1/50, 1/100, and 1/200.

13. The method according to claim 9, wherein said marker is selected from the group consisting of alkaline phosphatase, peroxidase, biotin, and chemiluminescence.

14. The method according to claim 10, wherein said biological fluid is plasma or serum.

15. The method according to claim 9, wherein between steps b) and c) non-specific binding sites to the membrane are blocked by incubating said membrane with non-specific proteins.

* * * * *